United States Patent [19]

Barratt et al.

[11] Patent Number: 5,493,021
[45] Date of Patent: Feb. 20, 1996

[54] PREPARATION OF LACTAMS

[75] Inventors: David Barratt, Ramsbottom Bury, Great Britain; Laurent Gilbert, Lyons, France

[73] Assignee: Rhone-Poulenc Chimie, Courbevoie, France

[21] Appl. No.: 360,623

[22] Filed: Dec. 21, 1994

[30] Foreign Application Priority Data

Dec. 23, 1993 [FR] France .................. 93 15775

[51] Int. Cl.⁶ .................. C07D 201/08
[52] U.S. Cl. .................. 540/539; 540/451; 546/243; 548/543
[58] Field of Search .................. 540/539, 451; 546/243; 548/543

[56] References Cited

U.S. PATENT DOCUMENTS 2,357,484  9/1944  Martin .................. 260/239
4,628,085  12/1986  Mares et al. .................. 260/239.3 A

FOREIGN PATENT DOCUMENTS 0150295  8/1985  European Pat. Off. .
2029540  10/1970  France .

OTHER PUBLICATIONS

Chemical Abstracts, vol. 74, No. 18, May 3, 1971, Columbus, Ohio, U.S.; Abstract No. 91756t, p. 271, col. 1 (abstract of JP-A-7,026,847).

*Primary Examiner*—Robert T. Bond
*Attorney, Agent, or Firm*—Burns, Doane, Swecker & Mathis

[57] ABSTRACT

Lactams, in particular epsilon-caprolactam (a basic starting material for the production of nylon 6), are selectively prepared by cyclizing/reacting the corresponding aminonitriles with water, in the presence of a catalytically effective amount of a deactivation-resistant solid metal phosphate having the general formula (II):

$$MH_h(PO_4)_n \cdot (Imp)_p$$

in which M is a divalent, trivalent, tetravalent or pentavalent element selected from among those of Groups 2a, 3b, 4b, 5b, 6b, 7b, 8, 2b, 3a, 4a and 5a of the Periodic Table, or mixture thereof, or M=0; Imp is a basic impregnating compound which comprises an alkali or alkaline earth metal, or mixture thereof, together with an electrical neutrality-ensuing counteranion therefor; n is 1, 2 or 3; h is 0, 1 or 2; and p is a number ranging from 0 to ⅓, corresponding to the molar ratio between the moiety Imp and the moiety $MH_h(PO_4)_n$.

20 Claims, No Drawings

PREPARATION OF LACTAMS

BACKGROUND OF THE INVENTION

1. Field of the Invention

The present invention relates to the preparation of lactams by ring-closing hydrolysis of the corresponding aminonitriles.

2. Description of the Prior Art

Aliphatic lactams, in particular epsilon-caprolactam are basic starting materials for the production of polyamides (e.g., polyamide 6 from caprolactam).

One known technique for preparing these lactams entails a ring-closing hydrolysis of the corresponding aminonitriles, more particularly of unbranched aliphatic aminonitriles, by passing them in vapor phase, with water, over a solid catalyst.

Thus, U.S. Pat. No. 2,357,484 describes a process for the vapor phase preparation of lactam, by passing a mixture of water and of aminonitrile over a dehydration catalyst such as activated alumina, silica gel and titanium dioxide or borophosphoric acid.

U.S. Pat. No. 4,628,085 discusses a process for the preparation of lactams in the vapor phase, by contacting an aliphatic or aromatic aminonitrile and water with a catalyst based on silica in the form of spherical particles which have a BET specific surface area greater than 250 m²/g and a mean pore diameter smaller than 20 nm, and generally in the presence of hydrogen and ammonia.

In general, the catalysts employed in the processes of the prior art enable good selectivity for the lactam to be attained. On the other hand, it is often the case that the catalysts are rapidly deactivated and this presents a serious drawback when carrying out the process on an industrial scale.

Moreover, the process described in U.S. Pat. No. 4,628,085 employs a very complex reaction mixture requiring, when the reaction is complete, separation and recycling operations which greatly complicate the process.

SUMMARY OF THE INVENTION

Accordingly, a major object of the present invention is the provision of novel catalysts for the conversion of aminonitriles into lactams, with good selectivity, such catalysts having longer useful lives and therefore requiring less frequent regeneration.

Briefly, the present invention features a process for the preparation of lactams, in vapor phase, by reacting an aliphatic aminonitrile having the general formula (I):

$$N\equiv C\text{-}R\text{-}NH_2 \qquad (I)$$

in which R is an alkylene radical having from 3 to 12 carbon atoms, with water, in the presence of a catalytically effective amount of a solid metal phosphate catalyst having the general formula (II):

$$MH_h(PO_4)_n \cdot (Imp)_p \qquad (II)$$

in which M is a divalent, trivalent, tetravalent or pentavalent element selected from among those of Groups 2a, 3b, 4b, 5b, 6b, 7b, 8, 2b, 3a, 4a and 5a of the Periodic Table, or mixture thereof, or M=0; Imp represents a basic impregnating compound comprising an alkali metal or alkaline earth metal, or mixture thereof, in combination with a counteranion to ensure electrical neutrality; n is 1, 2 or 3; h is 0, 1 or 2; and p is a number ranging from 0 to ⅓ and corresponds to a molar ratio of the impregnating compound IMP and the impregnated compound $MH_h(PO_4)_n$.

DETAILED DESCRIPTION OF BEST MODE AND PREFERRED EMBODIMENTS OF THE INVENTION

More particularly according to the present invention, the preferred aminonitriles of formula (I) are those which produce lactams that are used as raw materials for the preparation of polyamides 4, 5, 6 and 10, namely, those in the formula of which the symbol R is a linear alkylene radical having 3, 4, 5 or 9 carbon atoms. The most preferred compound of formula (I) is 6-aminocapronitrile (or epsilon-capronitrile), which produces caprolactam, the polymerization of which yields polyamide or nylon 6.

Among the metals of Groups 2a, 3b, 4b, 5b, 6b, 7b, 8, 2b, 3a, 4a and 5a of the Periodic Table, particularly representative are beryllium, magnesium, calcium, strontium, barium, aluminum, boron, gallium, indium, yttrium, lanthanides such as lanthanum, cerium, praseodymium, neodymium, samarium, europium, gadolinium, terbium, dysprosium, holmium, erbium, thulium, ytterbium and lutetium, zirconium, titanium, vanadium, niobium, iron, germanium, tin and bismuth.

Among the lanthanide phosphates, a first category may be distinguished, which includes the orthophosphates of light rare earths, also designated the ceric rare earths, including lanthanum, cerium, praseodymium, neodymium, samarium and europium. These orthophosphates are dimorphic. They have a hexagonal structure and evolve into a monoclinic structure when heated to a temperature of 600° C. to 800° C.

A second category of lanthanide phosphates includes gadolinium, terbium and dysprosium orthophosphates. These orthophosphates have the same structure as the orthophosphates of ceric rare earths but, in addition, have a third crystalline phase of tetragonal structure at high temperature (at about 1,7000° C.).

A third category of lanthanide phosphates includes the orthophosphates of heavy rare earths, also designated yttric rare earths, including yttrium, holmium, erbium, thulium, ytterbium and lutetium. These compounds crystallize only in the tetragonal form.

Among the aforesaid categories of rare earth orthophosphates, the ceric rare earth orthophosphates are the preferred.

Metal phosphates of formula (II) can be used that are mixtures of the phosphates of a plurality of the metals indicated above, or mixed phosphates of a plurality of the metals indicated above, or else mixed phosphates containing one or more of the metals indicated above and one or more other metals such as the alkali or alkaline earth metals.

The counteranoins constituting the impregnating compound Imp are basic. Particularly exemplary of such counteranoins are the hydroxide, phosphate, hydrogenphosphate, dihydrogenphosphate, chloride, fluoride, nitrate, benzoate and oxalate ions.

The molar ratio p preferably ranges from 0.02 to 0.2.

With respect to the general techniques for preparing the aforesaid phosphates (as described especially, in P. Pascal, Nouveau traité de chimie minérale, vol. X, pages 821–823

(1956) and in Gmelin's Handbuch der anorganischen Chemie (8th edition), volume 16 (C), pages 202–206 (1956)), two principal routes exist for preparing phosphates. On the one hand, a soluble salt of the metal (chloride, nitrate) is precipitated using ammonium hydrogenphosphate or phosphoric acid. On the other hand, the metal oxide or carbonate (which are insoluble) is dissolved using phosphoric acid, generally with heating, followed by a reprecipitation.

The precipitated phosphates obtained via either of these routes may be dried, treated with an organic base (such as aqueous ammonia) or an inorganic base (such as an alkali metal hydroxide) and then may be calcined, it being possible for these three operations to be carried out in the order shown or in a different order.

The metal phosphates of formula (II) in the event that the symbol p is greater than 0 may be prepared according to one of the techniques described above, with a solution or a suspension of Imp in a volatile solvent, such as, preferably, water.

The results are correspondingly better the more soluble Imp is and the more freshly produced is the compound $MH_h(PO_4)_n$.

Thus, one advantageous process for preparing the phosphates of formula (II) comprises:

(a) first synthesizing the compound $MH_h(PO_4)_n$ and then, preferably without isolating $MH_h(PO_4)_n$ from the reaction mixture;

(b) introducing the impregnating compound Imp into the reaction mixture;

(c) separating any residual liquid from the reaction solids; and (d) drying and optionally calcining the resulting product.

The performance of the catalyst of formula (II) and especially its resistance to deactivation can be further improved by calcination. The calcination temperature advantageously ranges from 300° C. to 1,000° C. and preferably from 400° C. to 900° C. The duration of the calcination may vary over wide limits, and generally ranges from 1 hour to 24 hours.

Among the preferred catalysts of formula (II) for the process of the invention, particularly representative are lanthanum phosphate, calcined lanthanum phosphate, lanthanum phosphate in combination with a cesium, rubidium or potassium compound, calcined cerium phosphate, cerium phosphate in combination with a cesium, rubidium or potassium compound, samarium phosphate in combination with a cesium, rubidium or potassium compound, aluminum phosphate, aluminum phosphate in combination with a cesium, rubidium or potassium compound, calcined niobium phosphate, niobium phosphate in combination with a cesium, rubidium or potassium compound, calcined zirconium hydrogenphosphate, and zirconium hydrogenphosphate in combination with a cesium, rubidium or potassium compound.

The catalyst is generally employed in the form of a powder, tablets, beads or extrudates, it being optionally possible for the shaping thereof to be carried out with the aid of a binder. In certain instances, it may be advantageous for a least a portion of the free volume of the reactor to be occupied by an inert solid such as, for example, quartz, in order to promote the vaporization and the dispersion of the reactants.

The ring-closing hydrolysis reaction requires the presence of water. The molar ratio of water to the aminonitrile introduced advantageously ranges from 0.5 to 50 and preferably from 1 to 20.

The aminonitrile and the water may be introduced in the form of their mixtures in the vapor state, or may be introduced separately into the reactor. A prevaporizaton of the reactants may be carried out, and subsequently passing these through a mixing chamber.

Any inert gas such as nitrogen, helium or argon may be employed as a carrier.

The temperature at which the process of the invention is carried out must be sufficient for the reactants to be entirely in the vapor state. It generally ranges from 200° C. to 540° C. and preferably from 250° C. to 400° C.

The contact time between the aminonitrile and the catalyst is not critical. It may vary, especially depending on the apparatus employed. Contact times of 1 to 200 seconds are preferred, and, more preferably, of 50 to 100 seconds.

Pressure is also not a critical parameter of the process. It is thus possible to operate at pressures of $10^{-3}$ bar to 200 bars. The subject process is preferably carried out at a pressure of 0.1 to 20 bars.

The use of a solvent which is inert under the conditions of the reaction, whereby the reaction is thus carried out in the liquid phase, is also within the scope of this invention. Exemplary such solvents include, for example, an alkane, a cycloalkane, an aromatic hydrocarbon, or halogenated derivatives thereof.

In order to further illustrate the present invention and the advantages thereof, the following specific examples are given, it being understood that same are intended only as illustrative and in nowise limitative.

EXAMPLES 1 to 6

Into a 20-ml cylindrical Pryex glass reactor, arranged vertically and fitted with means for heating, ports for the inlet and the outlet of the gas streams and with a system for injecting the reactants, were charged, in succession: 10 ml of quartz, 1 ml of the catalyst in the form of a powder having a particle size of from 0.8 to 1.25 micrometers (nature of the catalyst indicated in Table 1 below) and then an additional 10 ml of quartz.

Thus charged, the reactor was heated to 400° C. under a stream of air (at a flow rate of 1.5 liter/hour) for 2 hours. The reactor was then cooled to 320° C. (reaction temperature selected) and placed under a stream of nitrogen (flow rate of 1 liter/hour).

A mixture of 6-aminocapronitrile (ACN) and water (weight ratio 50/50, i.e., a water/ACN molar ratio of 6.2) was then injected into the reactor with the aid of a pump. The rate of injection of the mixture was 1.2 ml/h.

The vapor exiting the reactor was condensed in a glass trap at ambient temperature, for a time period of 2 hours.

The final reaction mixture was analyzed quantitatively by vapor phase chromatography.

The degree of conversion (DC) of aminocapronitrile, the yield (RY) of caprolactam (CPL) based on the aminocapronitrile converted, and the activity of the catalyst, measured in grams of caprolactam formed/milliliter of catalyst x hour were determined.

The results obtained are reported in Table 1 below:

TABLE 1

| Example | Catalyst | DC ACN % | RY CPL % | Activity |
|---|---|---|---|---|
| Example 1 | LaPO$_4$ | 63 | 91 | 0.49 g |
| Example 2 | LaPO$_4$, calcined 4 h at 700° C. | 90 | 92 | 0.47 g |
| Example 3 | LaPO$_4$/CS* | 69 | 97 | 0.63 g |
| Example 4 | AlPO$_4$ | 88 | 93 | 0.70 g |
| Example 5 | Zr(HPO$_4$)$_2$ | 45 | 77 | 0.32 g |
| Example 6 | NbOPO$_4$ | 39 | 100 | 0.33 g |

*La phosphate doped with Cs hydrogenphosphate (CS/LaPO$_4$ molar ratio = 0.053)

EXAMPLES 7 to 9

The procedures of Examples 1 to 3 were repeated, the change in the activity of the various catalysts being monitored, over periods of time of up to 35 hours.

The values of the activity are reported in Table 2 below for each catalyst and for increasing reaction periods (ND=value not determined).

TABLE 2

| | | Activity of the catalyst for time periods of | | | | | | |
|---|---|---|---|---|---|---|---|---|
| Example | Catalyst | 4 h | 6 h | 8 h | 10 h | 25 h | 30 h | 35 h |
| Example 7 | LaPO$_4$ | 0.45 | 0.40 | 0.35 | ND | ND | ND | ND |
| Example 8 | LaPO$_4$/Cs | 0.60 | 0.55 | 0.60 | 0.68 | 0.60 | 0.55 | 0.63 |
| Example 9 | Calcined LaPO$_4$ | 0.62 | 0.70 | 0.63 | 0.50 | 0.35 | 0.37 | 0.42 |

EXAMPLES 10 and 11

The procedure of Example 1 was repeated under the same conditions, but with the ring-closing hydrolysis reaction being carried out at different temperatures.

The results obtained are reported in Table 3 below, with the results of Example 1 being repeated for purposes of comparison.

TABLE 3

| Example | Temperature | DC ACN % | RY CPL % | Activity |
|---|---|---|---|---|
| Example 10 | 280° C. | 44 | 90 | 0.4 |
| Example 11 | 300° C. | 46 | 100 | 0.5 |
| Example 1 | 320° C. | 63 | 91 | 0.5 |

EXAMPLE 12 (Comparative)

The procedure of Example 1 was repeated, but with the La phosphate being replaced by silica (marketed under the trademark Aerosil 200) calcined for 16 h at 600° C.

The operating conditions were the same as in Example 1 (temperature of 320° C.; water/ACN molar ratio of 6.2; duration of 2 h).

The following results were obtained:

(a) DC of ACN: 17.6%

(b) RY of CPL: 53%

(c) Catalyst activity: 0.04 g CPL/ml catalyst xh.

The silica thus produced a low yield of caprolactam and exhibited an extremely low activity.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a lactam, comprising cyclizing/reacting the corresponding aminonitrile with water, in the presence of a catalytically effective amount of a solid metal phosphate having the general formula (II):

$$MH_h(PO_4)_n \cdot (Imp)_p \qquad (II)$$

in which M is a divalent, trivalent, tetravalent or pentavalent element selected from among those of Groups 2a, 3b, 4b, 5b, 6b, 7b, 8, 2b, 3a, 4a and 5a of the Periodic Table, or mixture thereof, or M=0; Imp is a basic impregnating compound which comprises an alkali or alkaline earth metal, or mixture thereof, together with an electrical neutrality-ensuing counteranion therefor; n is 1, 2 or 3; h is 0, 1 or 2; and p is a number ranging from 0 to ⅓, corresponding to the molar ratio between the moiety Imp and the moiety $MH_h(PO_4)_n$.

2. The process as defined by claim 1, carried out in the vapor phase and said corresponding aminonitrile having the formula ( I ):

$$N\equiv C-R-NH_2 \qquad (I)$$

in which R is an alkylene radical having from 3 to 12 carbon atoms.

3. The process as defined by claim 2, said aminonitrile of formula (I) comprising 6-aminocapronitrile.

4. The process as defined by claim 1, wherein formula (II), M is selected from among beryllium, magnesium, calcium, strontium, barium, aluminum, boron, gallium, indium, yttrium, lanthanum, cerium, praseodymium, neodymium, samarium, europium, gadolinium, terbium, dysprosium, holmium, erbium, thulium, ytterbium, lutetium, zirconium, titanium, vanadium, niobium, iron, germanium, tin and bismuth.

5. The process as defined by claim 2, wherein formula (I), R has 3, 4, 5 or 9 carbon atoms.

6. The process as defined by claim 1, said metal phosphate of formula (II) comprising a light rare earth orthophosphate.

7. The process as defined by claim 1, said metal phosphate of formula (II) comprising a heavy rare earth orthophosphate.

8. The process as defined by claim 1, said metal phosphate of formula (II) comprising a ceric rare earth orthophosphate.

9. The process as defined by claim 1, said metal phosphate of formula (II) comprising a lanthanide phosphate.

10. The process as defined by claim 1, said metal phosphate of formula (II) comprising a mixture of at least two different metal phosphates.

11. The process as defined by claim 1, said metal phosphate of formula (II) comprising at least one mixed phosphate.

12. The process as defined by claim 1, wherein formula (II), said counteranion comprises a hydroxide, phosphate, hydrogenphosphate, dihydrogenphosphate, chloride, fluoride, nitrate, benzoate or oxalate ion.

13. The process as defined by claim 1, wherein formula (II), p ranges from 0.02 to 0.2.

14. The process as defined by claim 1, said catalyst of formula (II) having been calcined at a temperature ranging from 300° C. to 1,000° C.

15. The process as defined by claim 1, said catalyst of formula (II) comprising lanthanum phosphate, calcined lanthanum phosphate, lanthanum phosphate combined with a cesium, rubidium or potassium compound, calcined cerium phosphate, cerium phosphate combined with a cesium, rubidium or potassium compound, samarium phosphate combined with a cesium, rubidium or potassium compound, aluminum phosphate, aluminum phosphate combined with a cesium, rubidium or potassium compound, calcined niobium phosphate, niobium phosphate combined with a cesium, rubidium or potassium compound, calcined zirconium hydrogenphosphate, or zirconium hydrogenphosphate combined with a cesium, rubidium or potassium compound.

16. The process as defined by claim 1, wherein the molar ratio of the water to said corresponding aminonitrile ranges from 0.5 to 50.

17. The process as defined by claim 16, said molar ratio ranging from 1 to 20.

18. The process as defined by claim 1, carried out at a temperature ranging from 200° C. to 450° C.

19. The process as defined by claim 18, carried out at a pressure ranging from $10^{-3}$ bar to 200 bar.

20. The process as defined by claim 19, carried out at a contact time ranging from 1 to 200 seconds.

* * * * *